United States Patent [19]
Englert et al.

[11] Patent Number: 5,652,268
[45] Date of Patent: Jul. 29, 1997

[54] SUBSTITUTED BENZENESULFONYLUREAS AND -THIOUREAS, PROCESSES FOR THEIR PREPARATION, THEIR USE AS A MEDICAMENT OR DIAGNOSTIC, AND MEDICAMENT CONTAINING THEM

[75] Inventors: Heinrich Englert, Hofheim; Uwe Gerlach, Hattersheim; Dieter Mania, Königstein; Heinz Gögelein; Joachim Kaiser, both of Frankfurt, all of Germany

[73] Assignee: Hoechst Aktiengesellschaft, Frankfurt am Main, Germany

[21] Appl. No.: 602,053

[22] Filed: Feb. 15, 1996

[30] Foreign Application Priority Data

Feb. 17, 1995 [DE] Germany ............... 195 05 397.4

[51] Int. Cl.$^6$ ............... A61K 31/64; A61K 31/17; C07C 275/00; C07C 273/00
[52] U.S. Cl. ............... 514/584; 514/592; 514/593; 514/821; 564/23; 564/25; 564/41; 564/64
[58] Field of Search ............... 564/23, 24, 25, 564/41, 64; 514/584, 592, 593, 821

[56] References Cited

FOREIGN PATENT DOCUMENTS

| | | |
|---|---|---|
| 0612724A1 | 8/1994 | European Pat. Off. . |
| 1518874C3 | 5/1970 | Germany . |
| 2413514A1 | 2/1976 | Germany . |

OTHER PUBLICATIONS

Derwent Abstract of DE-B-1 518 877, Jul. 4, 1974.
Derwent Abstract of DE-B-1 518 874, May 14, 1970.
Derwent Abstract of EP-A-612 724, Aug. 31, 1994.
Chemical Abstract of DE-A-1 518 874, May 14, 1970.

*Primary Examiner*—Shailendra Kumar
*Attorney, Agent, or Firm*—Finnegan, Henderson, Farabow, Garrett & Dunner, L.L.P.

[57] ABSTRACT

This invention relates to substituted benzenesulfonylureas and -thioureas, processes for their preparation, their use as a medicament or diagnostic, and medicament containing them.

Substituted benzenesulfonylureas and -thioureas 1

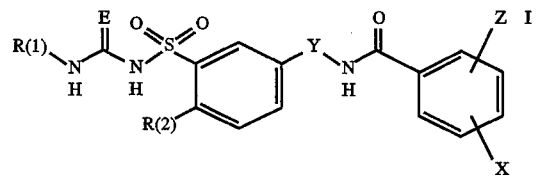

exhibit effects on the cardiovascular system.

13 Claims, No Drawings

SUBSTITUTED BENZENESULFONYLUREAS AND-THIOUREAS, PROCESSES FOR THEIR PREPARATION, THEIR USE AS A MEDICAMENT OR DIAGNOSTIC, AND MEDICAMENT CONTAINING THEM

DESCRIPTION

This invention relates to substituted benzenesulfonylureas and-thioureas, processes for their preparation, their use as a medicament or diagnostic, and medicament containing them.

The invention relates to substituted benzenesulfonylureas and -thioureas of the formula I

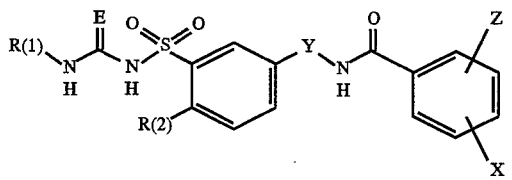

in which:

R(1) is hydrogen, methyl or trifluoromethyl;

R(2) is alkoxy having 4, 5, 6, 7, 8, 9 or 10 carbon atoms, where 1 to 6 carbon atoms are replaced by the heteroatoms O, S or NH;

E is oxygen or sulfur;

Y is $-[CR(3)_2]_{1-4}$;

R(3) is hydrogen or alkyl having 1 or 2 carbon atoms;

X is hydrogen, halogen or alkyl having 1, 2, 3, 4, 5 or 6 carbon atoms;

Z is nitro, halogen, alkoxy having 1, 2, 3 or 4 carbon atoms or alkyl having 1, 2, 3 or 4 carbon atoms;

and their pharmaceutically tolerable salts.

Sulfonylureas are disclosed in German Offenlegungsschrift 2 413 514 and German Patent 1 518 874. Their hypoglycemic action is described there. A prototype of such hypoglycemic sulfonylureas is glibenclamide, which is used therapeutically as an agent for the treatment of diabetes mellitus and serves in research as a much-regarded tool for the investigation of so-called ATP-sensitive potassium channels. In addition to its hypoglycemic action, glibenclamide additionally has other actions which could not be employed therapeutically until now, but which are all attributed to blockade of precisely these ATP-sensitive potassium channels. This includes, in particular, an antifibrillatory action on the heart. In the treatment of ventricular fibrillation or its preliminary stages, however, a simultaneous lowering of blood sugar would be undesirable or even dangerous since it can further worsen the condition of the patient.

In European Offenlegungsschrift 0 612 724 compounds having decreased hypoglycemic action are already described which, however, are still not adequate for many purposes. Compounds having a second heteroatom in the substituent R(2), however, are neither anticipated nor suggested there.

It was therefore the object of the present invention to synthesize compounds which have an equally good cardiac action as glibenclamide, but have no or distinctly less effect on the blood sugar in cardiac-active doses or concentrations than glibenclamide.

This aim was achieved by the compounds described at the outset.

Preferred compounds I are those in which:

R(1) is hydrogen, methyl or trifluoromethyl;

R(2) is alkoxy having 4, 5, 6, 7, 8, 9 or 10 carbon atoms, in which one to six carbon atoms are replaced by the heteroatoms O, NH or S;

E is oxygen or sulfur;

Y is a straight substituted or unsubstituted hydrocarbon radical of the formula: $-[CR(3)_2]_{1-4}$;

R(3) is hydrogen or alkyl having 1 or 2 carbon atoms;

X is hydrogen, chlorine, fluorine or alkyl having 1, 2, 3 or 4 carbon atoms;

Z is nitro, fluorine, chlorine, alkyl having 1, 2, 3 or 4 carbon atoms or alkoxy having 1, 2, 3 or 4 carbon atoms;

and their pharmaceutically acceptable salts.

Particularly preferred compounds I are those in which:

R(1) is hydrogen or methyl;

R(2) is alkoxy having 4, 5, 6, 7, 8, 9 or 10 carbon atoms in which 1 to 6 carbon atoms are replaced by the heteroatoms O, S or NH;

E is oxygen or sulfur;

Y is $-[CR(3)_2]_{1-4}$;

R(3) is hydrogen or alkyl having 1 or 2 carbon atoms;

X is hydrogen, fluorine, chlorine or alkyl having 1, 2, 3 or 4 carbon atoms;

Z is chlorine, fluorine, alkyl having 1, 2, 3 or 4 carbon atoms or alkoxy having 1, 2, 3 or 4 carbon atoms;

and their pharmaceutically acceptable salts.

Very particularly preferred compounds of the formula I are those in which:

R(1) is hydrogen or methyl;

R(2) is methoxyethoxy or methoxyethoxyethoxy;

E is oxygen or sulfur;

Y is $-[CR(3)_2]_{2-3}$;

R(3) is hydrogen or methyl;

X is hydrogen, fluorine, chlorine or alkyl having 1, 2 or 3 carbon atoms;

Z is fluorine, chlorine, alkyl having 1, 2 or 3 carbon atoms or alkoxy having 1, 2 or 3 carbon atoms;

and their pharmaceutically acceptable salts.

Alkyl means, if not expressly stated otherwise, straight-chain, branched or cyclic saturated hydrocarbon radicals having one to six carbon atoms. The alkoxy terminus is an ether substituent having a straight-chain, branched or cyclic saturated hydrocarbon radical of from 1 to 10 carbon atoms. Halogen substituents which can be employed are the elements fluorine, chlorine, bromine an iodine. The carbon atoms of the alkyl side chain Y and the alkoxy chain can be asymmetrically substituted.

At the same time, the invention relates to compounds of one or the other enantiomer and of a racemic mixture or mixtures of the two antipodes in different proportions. Furthermore, compounds having two centers of chirality in the alkyl side chain Y and the alkoxy chain can occur. In this case, the invention comprises both the individual antipodes per se, and a mixture of the two enantiomers in different proportions, as well as the associated meso compounds.

The compounds of the present invention are useful pharmaceuticals for the treatment of cardiac arrhythmias of all types of origin and for the prevention of sudden heart death due to arrhythmia and can therefore be used as antiarrhythmics. Examples of arrhythmic disorders of the heart are supraventricular arrhythmias such as, for example, atrial tachycardias, atrial flutters or paroxysmal supraventricular arrhythmias or ventricular arrhythmias such as ventricular extrasystoles, but in particular life-threatening ventricular tachycardias or the particularly dangerous ventricular fibrillation. They are suitable in particular for those cases where arrhythmias are the result of a constriction of a coronary vessel, such as occur, for example, in angina pectoris or during an acute cardiac infarct or as a chronic result of a cardiac infarct. They are therefore suitable, in particular, in postinfarct patients for the prevention of sudden heart death. Further syndromes in which arrhythmias of this type and/or sudden heart death due to arrhythmia play a part are, for example, cardiac insufficiency or cardiac hypertrophy as a result of a chronically raised blood pressure.

Moreover, the compounds can positively affect a decreased contractility of the heart. In this context, it can be a question of a disease-related relaxation of cardiac contractility such as, for example, in cardiac insufficiency but also of acute cases such as heart failure in the case of effects of shock. Likewise, in a heart transplantation, the heart, after operation has taken place, can resume its functional capacity more rapidly and more reliably. The same applies to operations on the heart which make necessary a temporary paralysis of heart activity by means of cardioplegic solutions.

Suitable experimental animals for the demonstration of such effects are, for example, mice, rats, guinea-pigs, rabbits, dogs, monkeys or pigs. The compounds can therefore be used as pharmaceutical active compounds in human and veterinary medicine. They can further be used as intermediates for the production of further pharmaceutical active compounds.

The invention furthermore relates to a process for the preparation of the compounds I, which comprises (a) reacting an aromatic sulfonamide of the formula II

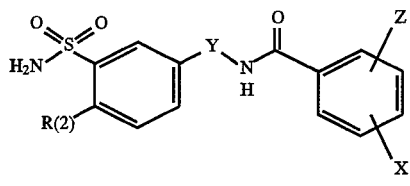

or its salt of the formula III

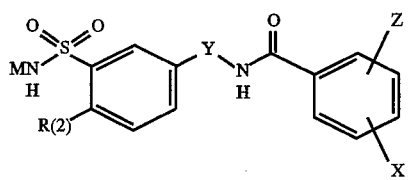

with an R(1)-substituted isocyanate of the formula IV

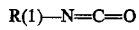

to give a substituted benzenesulfonylurea Ia.

Suitable cations M in the salts of the formula III are alkali metal, alkaline earth metal, ammonium and tetraalkylammonium ions. Equivalently to the R(1)-substituted isocyanates IV, R(1)-substituted carbamic acid esters, R(1)-substituted carbamic acid halides or R(1)-substituted ureas can be employed.

(b) An unsubstituted benzenesulfonylurea I [R(1)=H and E=O] can be prepared by reaction of an aromatic benzenesulfonamide of the formula II or its salt III with trialkylsilyl isocyanate or silicon tetraisocyanate and hydrolysis of the primary silicon-substituted benzenesulfonylureas. It is furthermore possible to prepare a benzenesulfonamide II or its salt III by reaction with a cyanogen halide and hydrolysis of the N-cyanosulfonamide primarily formed with mineral acids at temperatures from 0° C. to 100° C.

(c) Benzenesulfonylurea of the formula I where E is O can be prepared from an aromatic benzenesulfonamide II or its salts III using an R(1)-substituted trichloroacetamide of the formula V

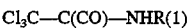

in the presence of a base in an inert solvent according to Synthesis 1987, 734–735 at temperatures from 25° C. to 150° C.

Suitable bases are, for example, alkali metal or alkaline earth metal hydroxides, hydrides, amides or alternatively alkoxides, such as sodium hydroxide, potassium hydroxide, calcium hydroxide, sodium hydride, potassium hydride, calcium hydride, sodium amide, potassium amide, sodium methoxide, sodium ethoxide, potassium methoxide or potassium ethoxide. Suitable inert solvents are ethers such as tetrahydrofuran, dioxane, ethylene glycol dimethyl ether (diglyme), ketones such as acetone or butanone, nitriles such as acetonitrile, nitro compounds such as nitromethane, esters such as ethyl acetate, amides such as dimethylformamide (DMF) or N-methylpyrrolidone (NMP), hexamethylphosphoramide, sulfoxides such as DMSO, sulfones such as sulfolane, and hydrocarbons such as benzene, toluene and xylenes. Furthermore, mixtures of these solvents with one another are also suitable.

(d) A benzenesulfonylthiourea I b

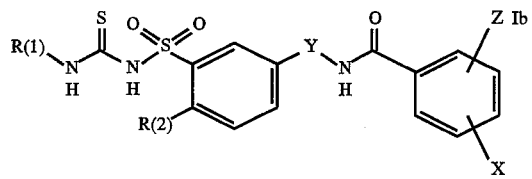

is prepared from a benzenesulfonamide II or its salt III and an R(1)-substituted isothiocyanate VI

An unsubstituted benzenesulfonylthiourea I b [R(1)=H] can be prepared by reaction of an aromatic benzenesulfonamide II or of its salt III with trimethylsilyl isothiocyanate or silicon tetraisothiocyanate and hydrolysis of the silicon-substituted benzenesulfonylurea primarily formed. It is furthermore possible to react an aromatic benzenesulfonamide II or its salt III with benzoyl isothiocyanate and to react the intermediate benzoyl-substituted benzenesulfonylthiourea with aqueous mineral acid to give I b [R(1)=H]. Similar processes are described in J. Med. Chem. 1992, 35, 1137–1144.

e) A substituted benzenesulfonylurea of the formula I where E is O can be prepared by transformation reaction of a benzenesulfonylthiourea of the structure I b. The replacement of the sulfur atom by an oxygen atom in the correspondingly substituted benzenesulfonylthioureas can be carried out, for example, with the aid of oxides or salts of heavy metals or alternatively by use of oxidants such as hydrogen peroxide, sodium peroxide or nitrous acid. Thioureas can also be desulfurized by treatment with phosgene or phosphorus pentachloride. As intermediates, chloroformic acid amidines or carbodiimides are obtained which are converted, for example, by hydrolysis or addition of water into the corresponding substituted benzenesulfonylureas. Isothioureas behave like thioureas in desulfurization and can accordingly also be used as starting substances for these reactions.

(f) A benzenesulfonylurea of the formula I where E is O can be prepared from a benzenesulfonyl halide of the formula VII

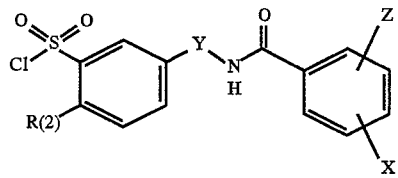 VII using an R(1)-substituted urea or an R(1)-substituted bis (trialkylsilyl)urea. The trialkylsilyl protective group can be removed from the resulting (trialkylsilyl) benzenesulfonylurea by standard methods. Furthermore, the sulfonyl chlorides VII can be reacted with parabanic acids to give benzenesulfonylparabanic acids, whose hydrolysis with mineral acids yields the corresponding benzenesulfonylureas I.

(g) A benzenesulfonylurea of the formula I where E is O can be prepared by reaction of an amine of the formula R(1)—NH$_2$ with a benzenesulfonyl isocyanate of the formula VIII

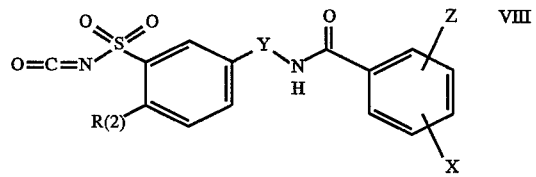 VIII

Likewise, amines R(1)—NH$_2$ can be reacted with benzenesulfonylcarbamic acid esters, -carbamic acid halides or benzenesulfonylureas I [where R(1)=H and E=O] to give the compounds I.

(h) A benzenesulfonylthiourea I b can be prepared by reaction of an amine of the formula R(1)—NH$_2$ with a benzenesulfonyl isothiocyanate of the formula IX

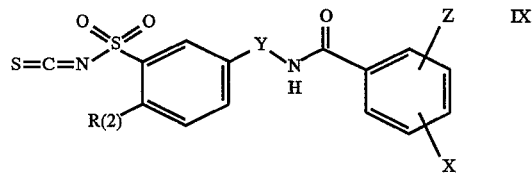 IX

Likewise, amines R(1)—NH$_2$ can be reacted with a benzenesulfonylcarbamic acid thioester or -carbamic acid thiohalide to give the compound I b.

(i) Correspondingly substituted benzenesulfenyl- or -sulfinylureas can be oxidized with oxidants such as hydrogen peroxide, sodium peroxide or nitrous acid to give benzenesulfonylureas of the formula I where E is O.

The compounds I and their physiologically acceptable salts are useful therapeutics which are suitable not only as antiarrhythmics, but also for prophylaxis in the case of disorders of the cardiovascular system, cardiac insufficiency, heart transplantation or cerebral vascular disorders in humans or mammals (for example apes, dogs, mice, rats, rabbits, guinea-pigs and cats).

Physiologically acceptable salts of the compounds I are understood according to Remmington's Pharmaceutical Science, 17th edition, 1985, pages 14–18 as meaning compounds of the formula XI

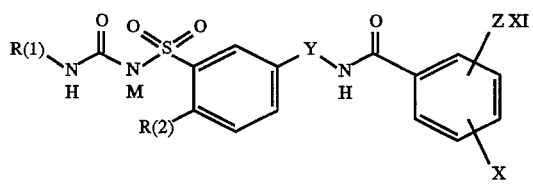 XI which can be prepared from nontoxic organic and inorganic bases and substituted benzenesulfonylureas I. In this context, salts are preferred in which M in the formula XI is sodium, potassium, rubidium, calcium, magnesium or ammonium ions, and can be the acid addition products of basic amino acids, such as lysine or arginine.

The starting compounds for the mentioned synthesis processes of the benzenesulfonylureas I are prepared by known methods, such as are described in the literature (for example in the standard works such as Houben-Weyl, Methoden der Organischen Chemie [Methods of Organic Chemistry], Georg Thieme Verlag, Stuttgart; Organic Reactions, John Wiley & Sons, Inc., New York; and in the patent applications indicated above), namely under reaction conditions which are known and suitable for the reactions mentioned. Use can also be made in this context of variants which are known but not mentioned here in greater detail. The starting substances can also, if desired, be formed in situ in such a way that they are not isolated from the reaction mixture, but immediately reacted further.

Scheme 1

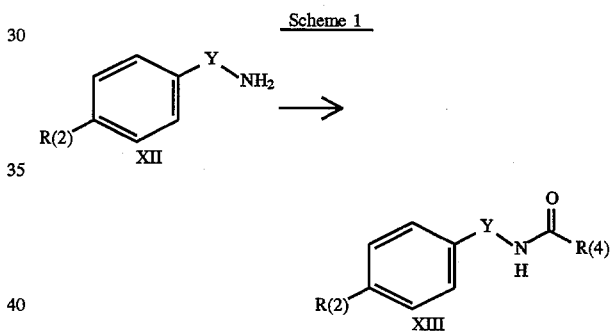

Suitably substituted amines of the formula XII can thus be acylated according to Scheme 1 and subjected to a halosulfonation. Suitable acylating agents for the acylation of amino groups are expediently the alkyl esters, halides (for example chlorides or bromides) or anhydrides of carboxylic acids of the formula R(4)—COB. R(4) is in this context a trihalomethyl radical, a (C$_1$–C$_4$)-alkyl radical or a benzoic acid derivative. The benzoic acid derivative can in this case be unsubstituted or substituted by one or two identical or different radicals X and Z. A possible substituent X is hydrogen, (C$_1$–C$_4$)-alkyl or halogen, a substituent Z is hydrogen, halogen, (C$_1$–C$_4$)-alkyl, (C$_1$–C$_4$)-alkoxy or nitro. B is a leaving group such as halide, (C$_1$–C$_4$)-alkoxy, trihaloacetate or (C$_1$–C$_4$)-carboxylate. Examples of this are acetic anhydride, trihaloacetic anhydride, acetyl halide, trihaloacetyl halide, propionyl chloride, isobutyryl bromide and chloride, formic acid/acetic anhydride, benzoyl chloride, 5-chloro-2-methoxybenzoyl chloride or -benzoic anhydride and —(C$_1$–C$_4$)-alkyl esters or 2,5-di-fluorobenzoyl chloride. The syntheses of the compound XIII are carried out with addition of a tertiary base such as pyridine or trialkylamines in the presence or absence of an inert solvent, it also being possible for a catalyst, such as dimethylaminopyridine, to be present. The reaction can be achieved at temperatures from approximately 0° C. to 160° C., preferably from 20° to 150°

C. The acyl group of the amines XII can be either a protective group, and, in the case of the benzoic acid derivatives, part of the compound I. Suitable inert solvents are ethers such as tetrahydrofuran, dioxane, glycol ethers such as ethylene glycol monomethyl or monoethyl ether (methyl glycol or ethyl glycol), ethylene glycol dimethyl ether (diglyme), ketones such as acetone or butanone, nitriles such as acetonitrile, nitro compounds such as nitromethane, esters such as ethyl acetate, amides such as dimethylformamide (DMF) or N-methylpyrrolidone (NMP), hexamethylphosphoramide, sulfoxides such as DMSO, chlorinated hydrocarbons such as dichloromethane, chloroform, trichloroethylene, 1,2-dichloroethane or carbon tetrachloride, and hydrocarbons such as benzene, toluene and xylenes. Furthermore, mixtures of these solvents with one another are also suitable.

Scheme 2

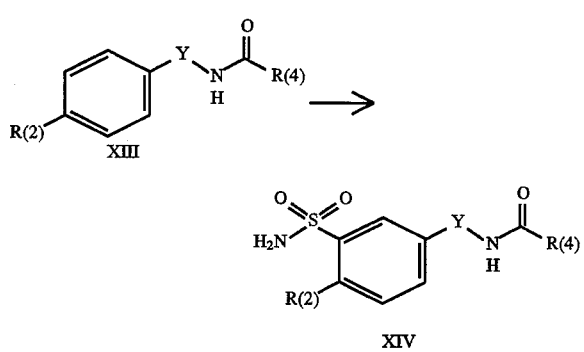

The amines XIII acylated according to Scheme 1 can be converted in a known manner according to Scheme 2 into the sulfonamides XIV. The sulfonamides XIV are prepared by known methods, namely under reaction conditions which are known and suitable for the reactions mentioned. In this case, use can also be made of variants which are known per se, but not mentioned here in greater detail. The syntheses can be carried out, if desired, in one, two or more steps. In particular, processes are preferred in which the acylated amine XII is converted by electrophilic reagents in the presence or absence of inert solvents at temperatures of −10° C. to 120° C., preferably of 0° C. to 100° C., into aromatic sulfonic acids and their derivatives, such as sulfonyl halides. For example, sulfonations can be carried out with sulfuric acids or oleum, halosulfonations with halosulfonic acids, reactions with sulfuryl halides in the presence of anhydrous metal halides or thionyl halides in the presence of anhydrous metal halides with subsequent oxidations, which are carried out in a known manner, to give aromatic sulfonyl chlorides. If sulfonic acids are the primary reaction products, these can be converted into sulfonyl halides in a known manner by acid halides, such as phosphorus trihalides, phosphorus pentahalides, phosphorus oxychloride, thionyl halides or oxalyl halides, either directly or by treatment with tertiary amines, such as pyridine or trialkylamines, or with alkali metal or alkaline earth metal hydroxides or reagents which form these basic compounds in situ. The sulfonic acid derivatives are converted into sulfonamides in a manner known from the literature, preferably sulfonyl chlorides are reacted with aqueous ammonia in inert solvents at temperatures from 0° C. to 100° C. Furthermore, aromatic sulfonamides can be synthesized according to processes described in the literature from the acylated amines of the formula XIII prepared according to Scheme 1 by reactions with organic reagents of alkali metals or alkaline earth metals in inert solvents and under an inert gas atmosphere at temperatures from −100° C. to 50° C., preferably from −100° C. to 30° C., with sulfur dioxide and subsequent thermal treatment with sulfamic acid.

If the acyl group functions as a protective group for the amine XIII, then this group can be removed with acids or bases after preparation of the sulfonamide XIV. By cleavage with aqueous acids or acids in inert solvents, the associated acid addition salt can be formed. Suitable for this reaction are, for example, sulfuric acid, nitric acid, halohydric acids, such as hydrochloric acid or hydrobromic acid, phosphoric acids such as orthophosphoric acid, sulfamic acid, and further organic acids, in particular aliphatic, alicyclic, araliphatic, aromatic or heterocyclic mono- or polybasic carboxylic, sulfonic or sulfuric acids, for example acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, phenylacetic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfonic acid. The cleavage of the acylated amine of the formula XIII with bases can be carried out in aqueous or inert solvents. Suitable bases are, for example, alkali metal or alkaline earth metal hydroxides, hydrides, amides or alternatively alkoxides, such as sodium hydroxide, potassium hydroxide, calcium hydroxide, sodium hydride, potassium hydride, calcium hydride, sodium amide, potassium amide, sodium methoxide, sodium ethoxide, potassium methoxide or potassium ethoxide.

The aromatic benzenesulfonamides of the formula III are prepared as mentioned above from the sulfonamide-substituted amines prepared in this way or their acid addition compounds. Depending on the nature of the members R(1), R(2), R(3), X, Y and Z, in individual cases one or the other of the processes mentioned will be unsuitable for the preparation of the compounds I or at least make precautions necessary for the protection of active groups. Comparatively rarely occurring cases of this type can be recognized by the person skilled in the art without difficulty, and it causes no difficulties in such cases to use another of the described synthetic routes successfully.

The compounds I can have one or more chiral centers. They can therefore be obtained during their preparation as racemates or, if optically active starting substances are used, alternatively in optically active form. If the compounds have two or more chiral centers, then they can be obtained during synthesis as mixtures of racemates, from which the individual isomers can be isolated in pure form, for example by recrystallizing from inert solvents. If desired, racemate which are obtained can be separated into their enantiomers mechanically or chemically by methods known per se. Diastereomers can thus be formed from the racemate by reaction with an optically active resolving agent. Suitable resolving agents for basic compounds are, for example, optically active acids, such as the R- or R,R- and S- or S,S-forms of tartaric acid, dibenzoyltartaric acid, diacetyltartaric acid, camphorsulfonic acids, mandelic acids, malic acid or lactic acid. Carbinols can further be amidated with the aid of chiral acylation reagents, for example R or S-α-methylbenzyl isocyanate, and then separated. The various forms of the diastereomers can be separated in a manner known per se, for example by fractional crystallization, and the enantiomers of the formula I can be liberated from the diastereomers in a known manner.

Resolution of enantiomers is also carried out by chromatography on optically active support materials.

The compounds I according to the invention and their physiologically acceptable salts can be used for the production of pharmaceutical preparations, in particular by a nonchemical route. In this context, they can be brought into a suitable dose form together with at least one solid or liquid excipient or auxiliary on their own or in combination with other pharmaceuticals having cardiovascular activity, such as calcium antagonists, NO donors or ACE inhibitors. These preparations can be used as pharmaceuticals in human or veterinary medicine. Possible excipients are organic or inorganic substances which are suitable for enteral (for example oral) or parenteral, for example intravenous, administration, or topical applications and do not react with the compounds I, for example water, vegetable oils, benzyl alcohols, polyethylene glycols, glycerol triacetate, gelatin, carbohydrates such as lactose or starch, magnesium stearate, talc, lanolin and petroleum jelly. In particular, tablets, coated tablets, capsules, syrups, juices or drops are used for oral administration, solutions, preferably oily or aqueous solutions, and further suspensions, emulsions or implants, are used for rectal administration, and ointments, creams, pastes, lotions, gels, sprays, foams, aerosols, solutions (for example in alcohols such as ethanol or isopropanol, acetonitrile, DMF, dimethylacetamide, 1,2-propanediol or their mixtures with one another or with water) or powders are used for topical application. The compounds I can also be lyophilized and the lyophilizates obtained used, for example, for the production of injection preparations. In particular for topical application, liposomal preparations are also suitable, which contain stabilizers and/or wetting agents, emulsifiers, salts and/or auxiliaries such as lubricants, preservatives, salts for affecting the osmotic pressure, buffer substances, colorants and flavorings and/or aromatic substances. If desired, they can also contain one or more further active compounds, for example one or more vitamins.

The doses which are necessary for the treatment of cardiac arrhythmias with the compounds I depend on whether the therapy is acute or prophylactic. Normally, a dose range of approximately at least 0.1 mg, preferably at least 1 mg, up to at most 100, preferably up to at most 10, mg per kg per day, based on an adult of weight of approximately 75 kg, is adequate if prophylaxis is conducted. The dose can in this case be divided as an oral or parenteral individual dose or else in up to four individual doses. If acute cases of cardiac arrhythmias are treated, for example in an intensive care unit, parenteral administration can be advantageous. A preferred dose range in critical situations can then be 10 to 100 mg and be administered, for example, as an intravenous continuous infusion.

According to the invention, in addition to the compounds described in the working examples, the compounds I compiled in the following Table can be obtained:

(1) 2-methoxy-5-chloro-{N-2-[-3-sulfonylamino-N-(methylaminocarbonyl)-4-methoxyethoxyphenyl]ethyl}benzamide (2) 2-methoxy-5-fluoro-{N-2-[-3-sulfonylamino-N-(methylaminocarbonyl)-4-methoxyethoxyphenyl]ethyl}benzamide (3) 2-methoxy-5-fluoro-{N-2-[-3-sulfonylamino-N-(methylaminothiocarbonyl)-4-methoxyethoxyphenyl]ethyl}benzamide

EXAMPLE 1

2-Methoxy-5-chloro-{N-2-[3-sulfonylammino-N-(methylaminothiocarbonyl)-4-methoxyethoxyphenyl]ethyl}benzamide

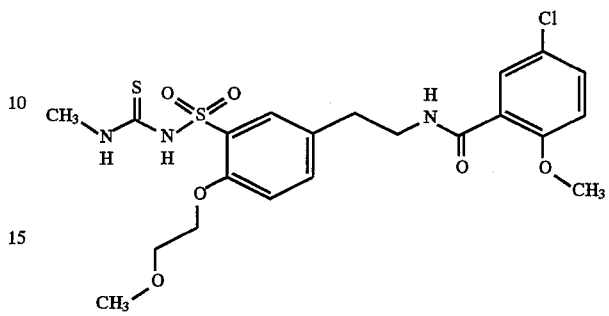

670 mg of 2-methoxy-5-chloro-{N-2-[3-sulfonylamino-4-methoxyethoxyphenyl]ethyl}benzamide were dissolved in 10 ml of absolute DMF and treated with 70 mg of 60% strength NaH. The mixture was stirred at room temperature for 20 min and 1.6 ml of a 1-molar methyl isothiocyanate solution in DMF were added dropwise. The reaction solution was heated at 80° C. for 1.5 h and added dropwise after cooling to 100 ml of 1N hydrochloric acid. It was extracted with ethyl acetate, the extract was dried and the solvent was removed in vacuo. The solid obtained was dissolved in a little hot ethanol and precipitated with water.

Yield 720 mg, m.p. 134° C.

EXAMPLE 2

2-Methoxy-5-chloro-{N-2-[3-sulfonylamino-N-(methylaminothiocarbonyl)-4-methoxyethoxyethoxyphenyl]ethyl}benzamide

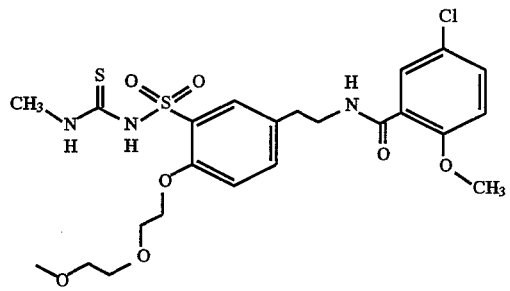

390 mg of 2-methoxy-5-chloro-{N-2-[3-sulfonylamino-4-methoxyethoxyethoxyphenyl]ethyl}benzamide were dissolved in 6 ml of DMF and treated with 35 mg of 60% strength NaH. The mixture was stirred at room temperature for 20 min and 0.8 ml of a 1-molar methyl isothiocyanate solution in DMF was added dropwise. The reaction solution was heated at 80° C. for 1.5 h and added dropwise after cooling to 50 ml of 1N hydrochloric acid. It was extracted with ethyl acetate, the extract was dried and the solvent was removed in vacuo.

M.p. 108° C.

Pharmacological data:

The therapeutic properties of the compounds I can be revealed using the following models:

(1) Action potential duration on the papillary muscle of the guinea-pig:

ATP deficiency states, as are observed during ischemia in the cardiac muscle cell, lead to a reduction of the action potential duration. They count as one of the causes of so-called reentry arrhythmias, which can cause sudden heart death. The opening of ATP-sensitive K channels as a result of the fall of ATP counts as causal here.

To measure the action potential, a standard microelectrode technique was employed. For this, guinea-pigs of both sexes were killed by a blow to the head, the hearts were removed, and the papillary muscles were separated out and suspended in an organ bath. The organ bath was irrigated with Ringer solution (0.9% NaCl, 0.048% KCl, 0.024% $CaCl_2$, 0.02% $NaHCO_3$ and 0.1% glucose) and aerated with a mixture of 95% oxygen and 5% carbon dioxide at a temperature of 36° C. The muscle was stimulated by means of an electrode using square-wave impulses of 1 V and 1 ms duration and a frequency of 2 Hz. The action potential was derived and recorded by means of a glass microelectrode inserted intracellularly, which was filled with 3 mM KCl solution. The substances to be tested were added to the Ringer solution in a concentration of $2.2 \times 10^{-5}$ mol per liter. The action potential was amplified using an amplifier from Hugo Sachs and shown on an oscilloscope. The duration of the action potential was determined at a degree of repolarization of 95% (APD95). Action potential reductions are produced either by addition of a 1 μM solution of the potassium channel opener Hoe 234 [J. Kaiser, H. G ögelein, Naunyn-Schmiedebergs Arch. Pharm. 1991, 343, R (59)] or by addition of 2-deoxyglucose. The action potential-reducing effect of these substances was prevented or reduced by the simultaneous addition of the test substances. Test substances were added to the bath solution as stock solutions in propanediol. The values indicated relate to measurements 30 minutes after addition. Glibenclamide was used in these measurements as a standard. The test concentration in all cases was $2 \times 10^{-6}$M.

The following values were measured:

| Example No. | APD95-start [ms] | APD95-30 min [ms] |
|---|---|---|
| 1 | 160 ± 13 | 150 ± 14 |

We claim:

1. A substituted benzenesulfonylurea or benzenesulfonylthiourea of the formula I

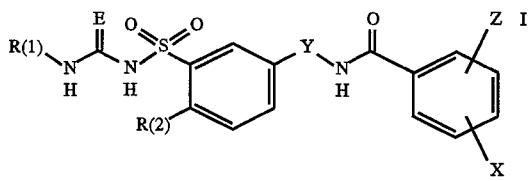

in which:

R(1) is hydrogen, methyl or trifluoromethyl;

R(2) is alkoxy having 4, 5, 6, 7, 8, 9 or 10 carbon atoms, where 1 to 6 carbon atoms are replaced by O, S or NH;

E is oxygen or sulfur;

Y is —$[CR(3)_2]_{1-4}$;

R(3) is hydrogen or alkyl having 1 or 2 carbon atoms;

X is hydrogen, halogen or alkyl having 1, 2, 3, 4, 5 or 6 carbon atoms;

Z is nitro, halogen, alkoxy having 1, 2, 3 or 4 carbon atoms or alkyl having 1, 2, 3 or 4 carbon atoms;

or its pharmaceutically acceptable salts.

2. A compound of the formula I as claimed in claim 1, wherein:

R(1) is hydrogen, methyl or trifluoromethyl;

R(2) is alkoxy having 4, 5, 6, 7, 8, 9 or 10 carbon atoms, in which one to six carbon atoms are replaced by O, NH or S;

E is oxygen or sulfur;

Y is a straight substituted or unsubstituted hydrocarbon radical of the formula:

—$[CR(3)_2]_{1-4}$;

R(3) is hydrogen or alkyl having 1 or 2 carbon atoms;

X is hydrogen, chlorine, fluorine or alkyl having 1, 2, 3 or 4 carbon atoms;

Z is nitro, fluorine, chlorine, alkyl having 1, 2, 3 or 4 carbon atoms or alkoxy having 1, 2, 3 or 4 carbon atoms.

3. A compound of the formula I as claimed in claim 1, wherein:

R(1) is hydrogen or methyl;

R(2) is alkoxy having 4, 5, 6, 7, 8, 9 or 10 carbon atoms, in which 1 to 6 carbon atoms are replaced by O, S or NH;

E is oxygen or sulfur;

Y is —$[CR(3)_2]_{1-4}$;

R(3) is hydrogen or alkyl having 1 or 2 carbon atoms;

X is hydrogen, fluorine, chlorine or alkyl having 1, 2, 3 or 4 carbon atoms;

Z is chlorine, fluorine, alkyl having 1, 2, 3 or 4 carbon atoms or alkoxy having 1, 2, 3 or 4 carbon atoms.

4. A compound of the formula I as claimed in claim 1, wherein:

R(1) is hydrogen or methyl;

R(2) is methoxyethoxy or methoxyethoxyethoxy;

E is oxygen or sulfur;

Y is —$[CR(3)_2]_{2-3}$;

R(3) is hydrogen or methyl;

X is hydrogen, fluorine, chlorine or alkyl having 1, 2 or 3 carbon atoms;

Z is fluorine, chlorine, alkyl having 1, 2 or 3 carbon atoms or alkoxy having 1, 2 or 3 carbon atoms.

5. A process for the preparation of a compound I as claimed in claim 1, which comprises (a) reacting an aromatic sulfonamide of the formula II

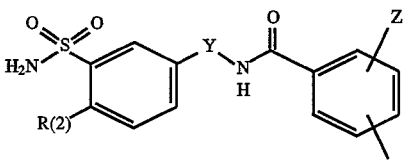

or its salt of the formula III

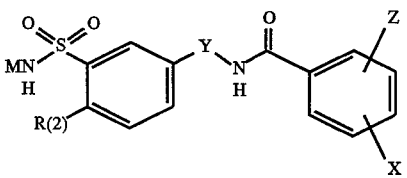

with an R(1)-substituted isocyanate of the formula IV

R(1)—N=C=O      IV where R(1), R(2), X, Y and Z have the meanings indicated in claim 1 and where M is an alkali metal, alkaline earth metal, ammonium or tetraalkylammonium ion to form a benzensulfonylurea of the formula I where E is O;

or (b) reacting an aromatic benzenesulfonamide of the formula II or its salt of the formula III with a trialkylsilyl isocyanate or silicon tetraisocyanate to form a primary silicon-substituted benzensulfonylurea and then hydrolyzing the primary silicon-substituted benzenesulfonylurea to form a benzenesulfonylurea of the formula I where E is O and R(1) is H;

or (c) reacting an aromatic benzenesulfonamide II or its salt of the formula III with an R(1)-substituted trichloroacetamide of the formula V

Cl₃C—C(CO)—NHR(1)    V in the presence of a base to form a benzenesulfonylurea of the formula I where E is O;

or (d) reacting a benzenesulfonamide II or its salt of the formula III and an R(1)-substituted isothiocyanate VI

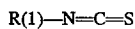

R(1)—N=C=S    VI:

to form a benzenesulfonylthiourea of the formula I where E is S;

or (e) reacting a benzenesulfonyl halide of the formula VII

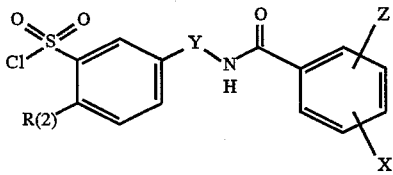

with an R(1)-substituted urea or an R(1)-substituted bis(trialkylsilyl)urea to form a benzenesulfonylurea of the formula I where E is O;

or (f) reacting an amine of the formula R(1)—NH₂ with a benzenesulfonyl isocyanate of the formula VIII

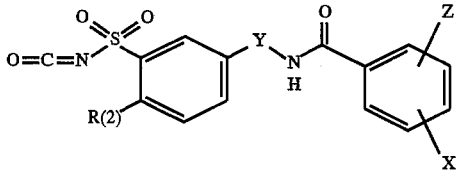

to form a benzenesulfonylurea of the formula I where E is O;

or (g) reacting an amine of the formula R(1)—NH₂ with a benzenesulfonyl isothiocyanate of the formula IX

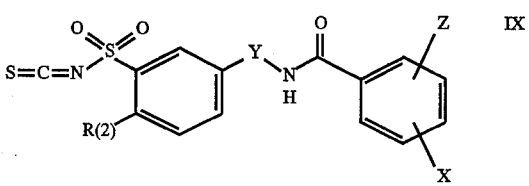

to form a benzenesulfonylthiourea of the formula I where E is S;

or (h) oxidizing a substituted benzenesulfenyl- or -sulfinylurea to give a benzenesulfonylurea of the formula I where E is O and optionally converting it into the pharmaceutically acceptable salt.

6. A process for the preparation of a compound I as claimed in claim 1, where E is O comprising the steps of desulfurizing a compound of the Formula I b

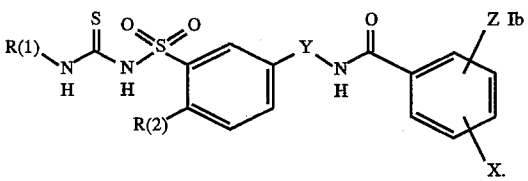

7. A process for the preparation of a compound I as claimed in claim 6, wherein a compound of the formula I b is reacted with oxides or salts of heavy metals.

8. A process for the preparation of a compound I as claimed in claim 6, wherein a compound of the formula I b is reacted with an oxidant.

9. A process for the preparation of a compound I as claimed in claim 8, wherein said oxidant is selected from the group consisting of hydrogen peroxide, sodium peroxide, and nitrous acid.

10. A process for the preparation of a compound I as claimed in claim 6, wherein a compound of the formula I b is reacted with phosgene or phosphorus pentachloride and then hydrolyzed to form said compound I.

11. A method for the treatment of cardiac arrhythmias, ischemic conditions of the heart, or weakened cardiac power, comprising administering an effective amount of a compound of the formula I as claimed in claim 1.

12. A method for the prevention of sudden heart death, comprising administering an effective amount of a compound of the formula I as claimed in claim 1.

13. A pharmaceutical composition, comprising an effective amount of a compound of the formula I as claimed in claim 1.

* * * * *